(12) United States Patent
Berger et al.

(10) Patent No.: US 7,284,885 B2
(45) Date of Patent: Oct. 23, 2007

(54) UV LAMP ARRANGEMENT AND ITS USE

(75) Inventors: Ulrich Berger, Biebergemünd (DE); Jürgen Lang, Frankfurt (DE); Stefan Greif, Fulda (DE); Bernd Ullrich, Erlensee (DE); Ernst Smolka, Goldbach (DE)

(73) Assignee: Heraeus Noblelight GmbH, Hanau (DE)

( * ) Notice: Subject to any disclaimer, the term of this patent is extended or adjusted under 35 U.S.C. 154(b) by 0 days.

(21) Appl. No.: 10/955,757

(22) Filed: Sep. 30, 2004

(65) Prior Publication Data
US 2005/0073843 A1 Apr. 7, 2005

(30) Foreign Application Priority Data
Oct. 1, 2003 (DE) ................. 103 46 131

(51) Int. Cl.
*F21V 17/06* (2006.01)
(52) U.S. Cl. ........................................ 362/437
(58) Field of Classification Search ........... 362/647, 362/649, 280, 437, 438, 439
See application file for complete search history.

(56) References Cited

U.S. PATENT DOCUMENTS

| 1,910,542 A | * | 5/1933 | Hendee | 362/433 |
| 4,309,616 A | * | 1/1982 | Wolff | 250/494.1 |
| 4,928,040 A | * | 5/1990 | Uesaki | 315/248 |
| 6,590,220 B1 | * | 7/2003 | Kalley et al. | 250/504 H |
| 6,717,164 B2 | * | 4/2004 | Ullrich et al. | 250/504 R |
| 2002/0067109 A1 | * | 6/2002 | Spiro et al. | 313/113 |
| 2003/0057813 A1 | * | 3/2003 | Mayer et al. | 313/113 |
| 2004/0061079 A1 | * | 4/2004 | Thompson et al. | 250/492.22 |

FOREIGN PATENT DOCUMENTS

| DE | 32 00 031 C2 | 3/1991 |
| DE | 39 37 256 A1 | 5/1991 |
| DE | 201 06 885 U1 | 8/2001 |
| DE | 101 20 740 A1 | 11/2002 |
| EP | 0 301 208 A2 | 2/1989 |
| EP | 529356 A1 * | 3/1993 |
| JP | 08306217 A * | 11/1996 |
| WO | WO97/32158 A1 | 9/1997 |

* cited by examiner

*Primary Examiner*—Renee Luebke
*Assistant Examiner*—Mary Zettl
(74) *Attorney, Agent, or Firm*—Akin Gump Strauss Hauer & Feld LLP

(57) ABSTRACT

A lamp arrangement is provided having a lamp socket, a concave reflector body arranged on the lamp socket, an emitter arranged within the cavity of the reflector body and on the lamp socket, and preferably a filter disk, which covers an outlet opening of the reflector body for radiation. The reflector body is detachably connected with the lamp socket by a bayonet catch. Alternatively, the reflector body can be connected with the lamp socket by at least two gripping arms. The lamp arrangement is designed especially for use in the UV range.

12 Claims, 15 Drawing Sheets

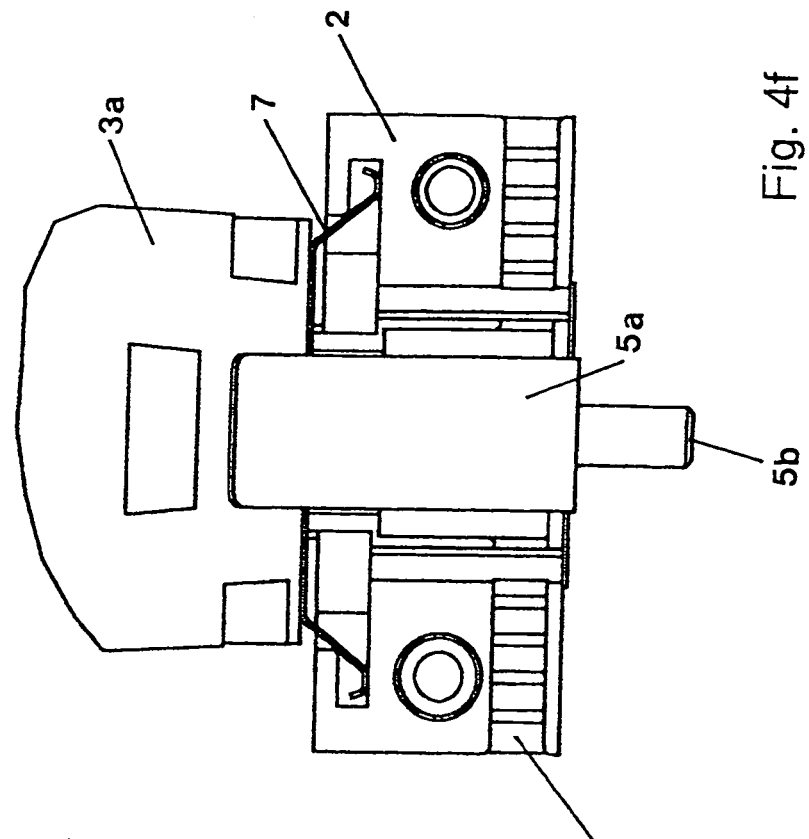
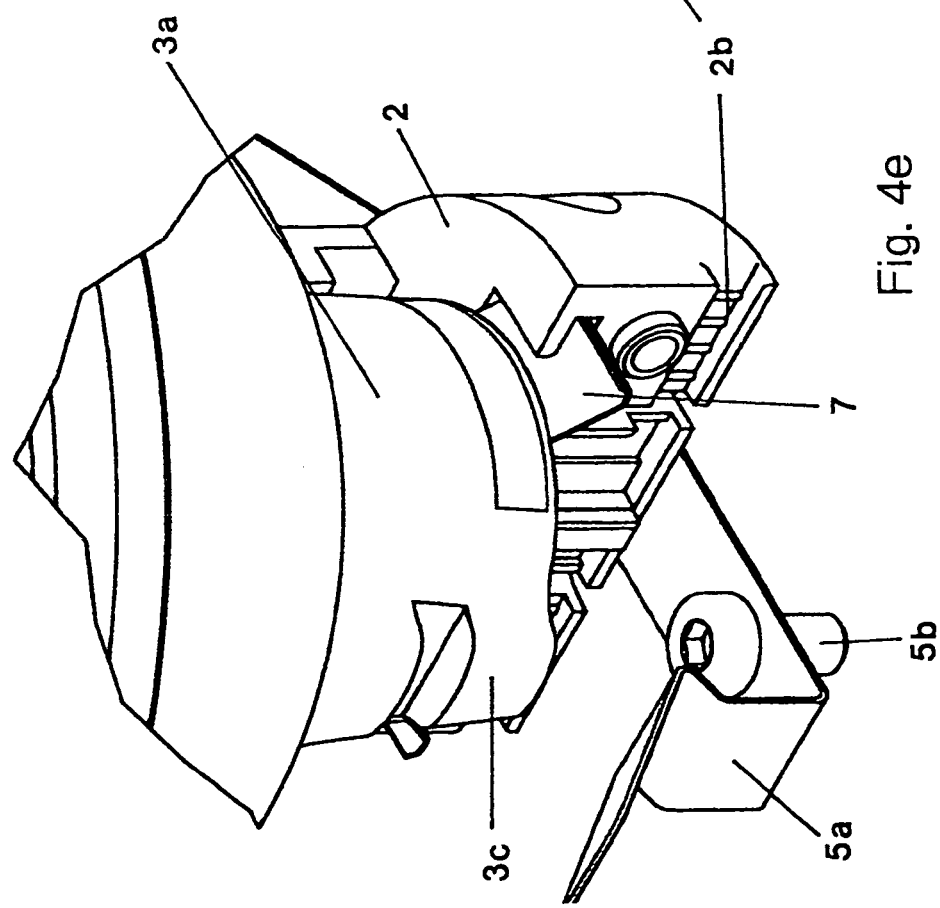

UV LAMP ARRANGEMENT AND ITS USE

BACKGROUND OF THE INVENTION

The invention relates to a UV lamp arrangement having a lamp socket, with a concave reflector body arranged on the lamp socket, with a UV emitter arranged within the cavity of the reflector body and on the lamp socket, and especially with a filter disk, which covers an outlet opening of the reflector body for UV radiation. The invention further relates to a use of this UV lamp arrangement.

Such lamp arrangements are known from International application publication WO 97/32158 for tanning devices. In a glass bulb, which is coated inside with a reflective coating, a mercury-vapor high-pressure lamp is arranged upright as a tanning lamp. The glass bulb is closed by a UV filter. The filter and/or the tanning lamp is exchangeable herein. Accordingly, in order to be able to evacuate the glass bulb in the lamp arrangement disclosed here, the glass bulb must be closed air-tight by seals with the tanning lamp and the UV filter. Thus, changing the UV filter or the lamp has proven to be problematic in terms of a new seal.

Published European patent application EP 301 208 A2 discloses a bayonet socket for a lamp or a reflector, wherein the bayonet catch fixes the lamp socket in a lamp fixture. Between the reflector and the bayonet socket, plug or clamp connections are disclosed, which allow the reflector to be detachable from the socket.

German utility model application DE 201 06 885U1 likewise discloses a lamp with a bayonet socket, wherein the bayonet catch fixes the socket in a lamp fixture. The lamp has a lamp bulb that can be unscrewed from the bayonet socket.

BRIEF SUMMARY OF THE INVENTION

It is now an object of the invention to provide a UV lamp system of the type described at the outset, in which the exchange of the tanning lamp can be carried out more simply and more problem-free, which further permits the reuse of the remaining parts of the UV lamp system.

The object is achieved in that the reflector body is detachably connected with the lamp socket by a bayonet catch. By such a construction of the lamp arrangement the reflector body, optionally including a filter glass disk, can be removed by a simple handle, so that the emitter is directly accessible. Now, it is possible to either exchange the emitter alone or to replace this including the socket. The reflector body and an optional filter disk arranged thereon can be reused.

The object is also achieved in that the reflector body is connected with the lamp socket by at least two gripping arms. Such a construction, like the bayonet catch, enables a simple exchange of the UV emitter when it fails and the reuse of all of the remaining components, such as reflector, filter glass disk, lamp socket, electrical connections, and gripping arms.

The solution according to the invention is suitable for all lamp arrangements used for optical radiation. For this purpose, optical radiation can be generated with an emitter. If the emitter has its maximum wavelength in the visible (VIS) or infra-red (IR) range, then it is a VIS or IR lamp arrangement with a VIS or IR emitter, whose reflector preferably has a VIS or IR reflective coating. The reflector can optionally be transparent to UV radiation. In particular, the lamp arrangement is provided for UV radiation, which is generated with a UV emitter.

It has proven advantageous if the reflector body has a reflector neck and the reflector neck is detachably connected with the lamp socket by the bayonet catch or if the reflector body is detachably connected with the lamp socket at the emitter opening of the reflector by a bayonet catch or with gripping arms.

Preferably, the reflector body is formed of glass, glass ceramic, ceramic, or metal. The reflector body preferably has a UV radiation-reflective coating.

In particular, it has proven advantageous if the reflector body is formed of glass or glass ceramic and its coating is transparent to infrared radiation. Thus, heat is transported away from the reflector body and cooling of the reflector body can be omitted.

It has proven advantageous if the reflector body has facets. Furthermore, it has proven advantageous if the UV radiation-reflective coating of the reflector body contains at least one metal oxide.

It is advantageous if the filter disk is connected with the reflector body by an elastic adhesive. Preferably, an elastic adhesive based on silicon is selected.

Here, it is preferable that the filter disk be connected with the reflector body such that there are still openings, through which air can be exchanged between the space outside the reflector body and the space inside the reflector body. It has proven advantageous if the reflector body has at least one half moon-shaped recess in the region of the outlet opening on its periphery.

However, it is just as possible for the filter disk to completely close the outlet opening of the reflector body.

It has proven advantageous if the lamp socket is formed of ceramic, plastic, or metal. Here, ceramic is especially preferred, because it is not only resistant to high temperatures but is also electrically insulating, so that the electrical connections for the UV emitter need not be specially insulated electrically from the socket.

Furthermore, it has proven favorable if the reflector body is formed of borosilicate glass or lime-sodium bicarbonate glass.

It is especially preferred if the reflector neck and the reflector body are formed of the same material and in one piece, wherein knobs are formed on the reflector neck, so that it can be connected directly with the lamp socket.

However, it is just as possible for the reflector neck and the reflector body to be formed of the same material and in one piece, wherein the reflector neck is connected with another component constructed as a ring, on which knobs are formed, so that the ring can be connected directly with the lamp socket. Here, the ring can be formed of metal, plastic, or ceramic.

It has proven advantageous if the ring is connected with the reflector neck by glass solder or adhesive or if the ring is shrunk onto the reflector neck. One-component adhesives as well as multiple-component adhesives are suitable for this purpose. It is especially preferred if the adhesive is an inorganic adhesive, such as a high temperature inorganic ceramic cement available from Sauereisen (Pittsburgh, Pa.), or if the adhesive is silicon-based.

It is especially favorable if the gripping arms are formed of bent wire or bent strips of sheet metal.

Preferably, a metal halide emitter is used as the UV emitter. Here, the UV emitter preferably has a lamp bulb made of quartz glass and also electrical contacts, which are led gas-tight through this bulb, either on one side or on opposing sides.

Use of the UV lamp arrangement according to the invention in a power range of about 100 W to 300 W without forced-air cooling is ideal. Here, the use of at least one UV lamp arrangement in a tanning device is especially preferred. It has proven advantageous here if the at least one UV lamp arrangement is mounted in the tanning device by two retaining screws, which are arranged at a spacing of about 25-27 mm from each other.

It has further proven advantageous if at least one UV lamp arrangement is mounted in the tanning device by two retaining screws, which are arranged at a spacing of about 29-31 mm from each other.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown.

In the drawings, FIGS. 1a to 12 explain the UV lamp arrangement according to the invention by way of example. FIGS. 1 to 6b relate to the bayonet catch, while FIGS. 7 to 12 relate to embodiments with gripping arms.

FIGS. 4a-4f show different views of another UV lamp arrangement of the invention with a round lamp socket, wherein only one half of the lamp socket is shown;

FIGS. 6a-6b show another UV lamp arrangement of the invention with an elongated lamp socket in views with and without reflector;

DETAILED DESCRIPTION OF THE INVENTION

Figure 1A:
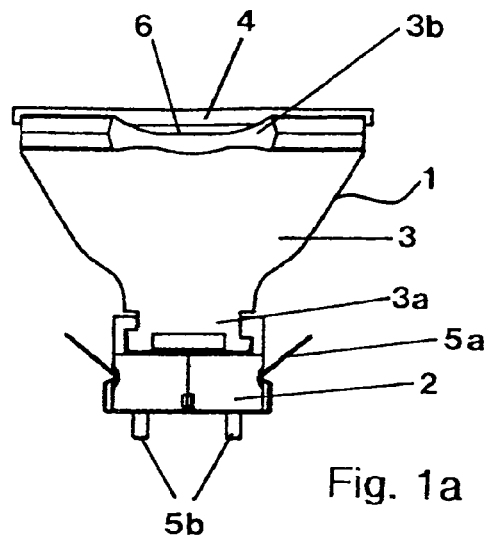
FIGS. 1a-1e show different views of a UV lamp arrangement of the invention with a rectangular lamp socket.

FIG. 1a shows a UV lamp arrangement 1 in the side view with a two-part, rectangular lamp socket 2 and a reflector body 3 made of glass. The outlet opening of the reflector body 3 for UV radiation is covered with a filter disk 4. Furthermore, the reflector body 3 has a reflector neck 3a, which is connected directly to the lamp socket 2 by a bayonet catch. In addition, in the region of the outlet opening of the reflector body 3 for UV radiation, there are half moon-shaped recesses 3b, such that openings 6 enable an exchange of air with the space in the reflector body 3. A spring 5a and also retaining screws 5b for mounting the UV lamp arrangement 1 in a tanning device are provided on the lamp socket 2.

Figure 1B:
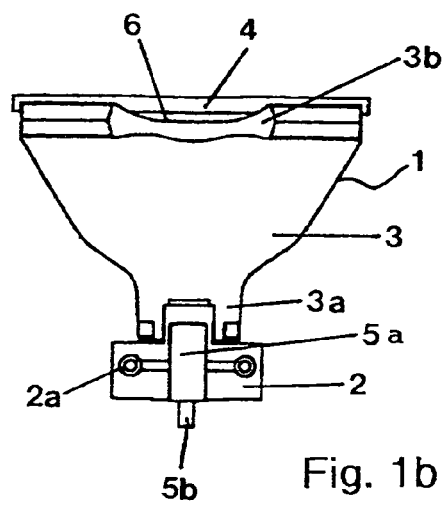

FIG. 1b shows the UV lamp arrangement 1 of FIG. 1 in another side view, but rotated by 90°. It can be seen that the two parts of the two-part lamp socket 2 are connected by rivets or screws 2a.

Figure 1C:
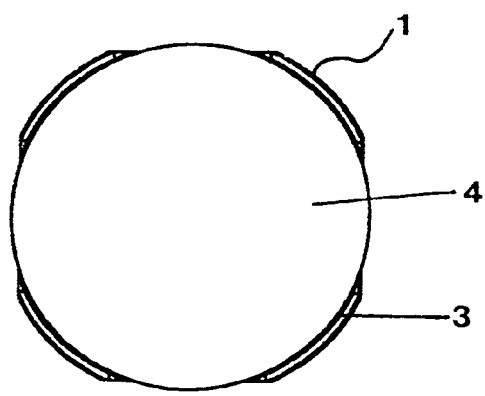

FIG. 1c shows the UV lamp arrangement 1 of FIGS. 1a and 1b in a top view.

Figure 1D:
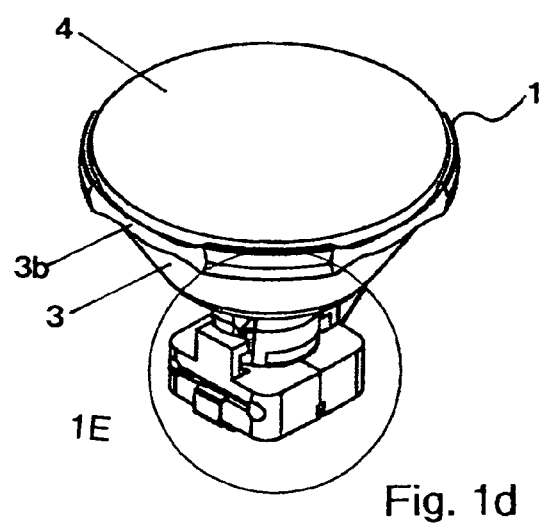

FIG. 1d shows the UV lamp arrangement 1 of FIGS. 1a-1c in a perspective view.

Figure 1E:
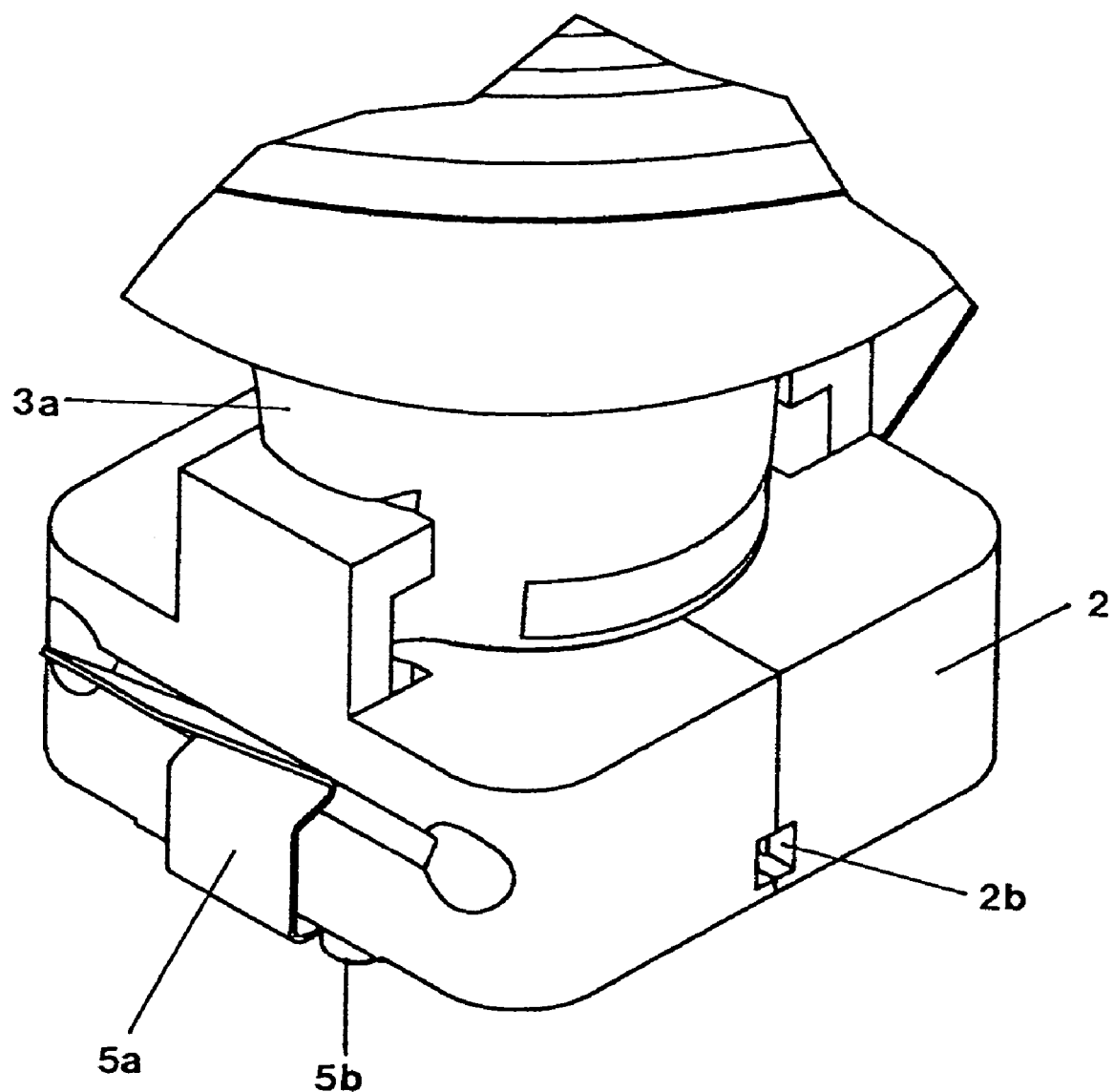

FIG. 1e shows the portion 1E of FIG. 1d in an enlarged view. Here, the bayonet catch between the reflector neck 3a and the lamp socket 2 can be seen clearly. Furthermore, there are openings 2b in the lamp socket 2, through which electrical connections of a UV emitter (not seen here but arranged in the reflector body 3) are guided to both sides of the lamp socket 2.

Figure 2A:
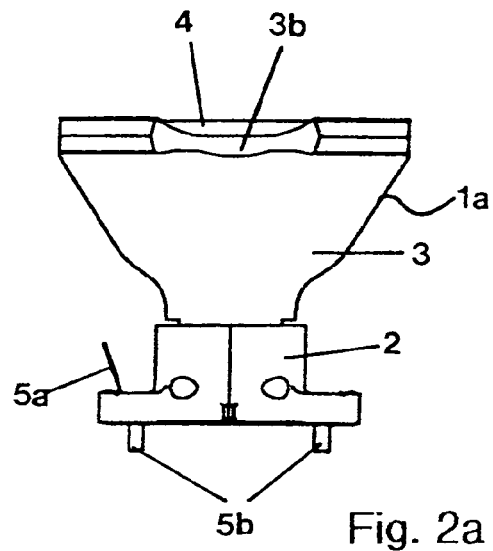
FIGS. 2a-2e show different views of another UV lamp arrangement of the invention with a round lamp socket.

FIG. 2a shows another UV lamp arrangement 1a in a side view with a two-part, round lamp socket 2 and a reflector body 3 made of glass. The outlet opening of the reflector body 3 for UV radiation is covered with a filter disk 4. Furthermore, the reflector body 3 has a reflector neck 3a, which is connected with the lamp socket 2 directly by a bayonet catch. In addition, in the region of the outlet opening of the reflector body 3 for UV radiation, there are half moon-shaped recesses 3b. Here, the filter disk 4 completely covers the reflector body 3, so that no opening remains. A spring 5a and also retaining screws 5b for mounting the UV lamp arrangement 1a in a tanning device are present on the lamp socket 2.

Figure 2B:
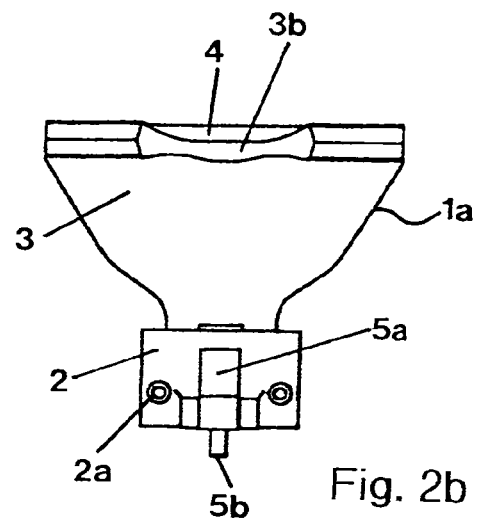

FIG. 2b shows the UV lamp arrangement 1a of FIG. 2a in another side view, but rotated by 90°. Here it can be seen that the two parts of the two-part lamp socket 2 are connected by rivets or screws 2a.

Figure 2C:
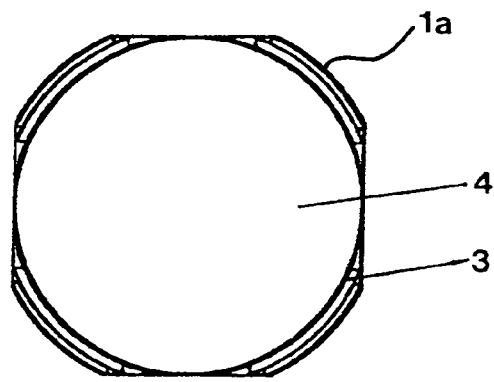

FIG. 2c shows the UV lamp arrangement 1a of FIGS. 2a and 2b in a top view.

Figure 2D:
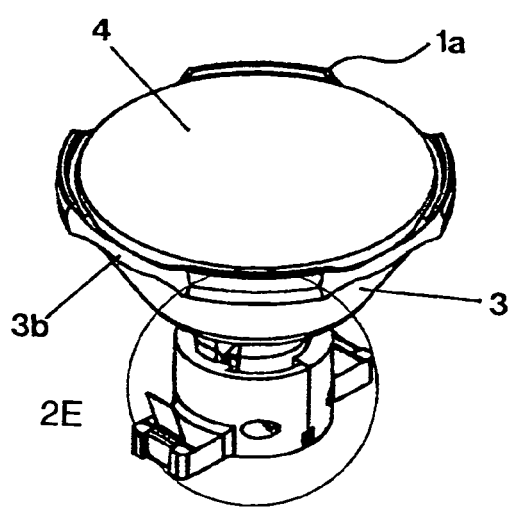

FIG. 2d shows the UV lamp arrangement 1a of FIGS. 2a-2c in a perspective view.

Figure 2E:
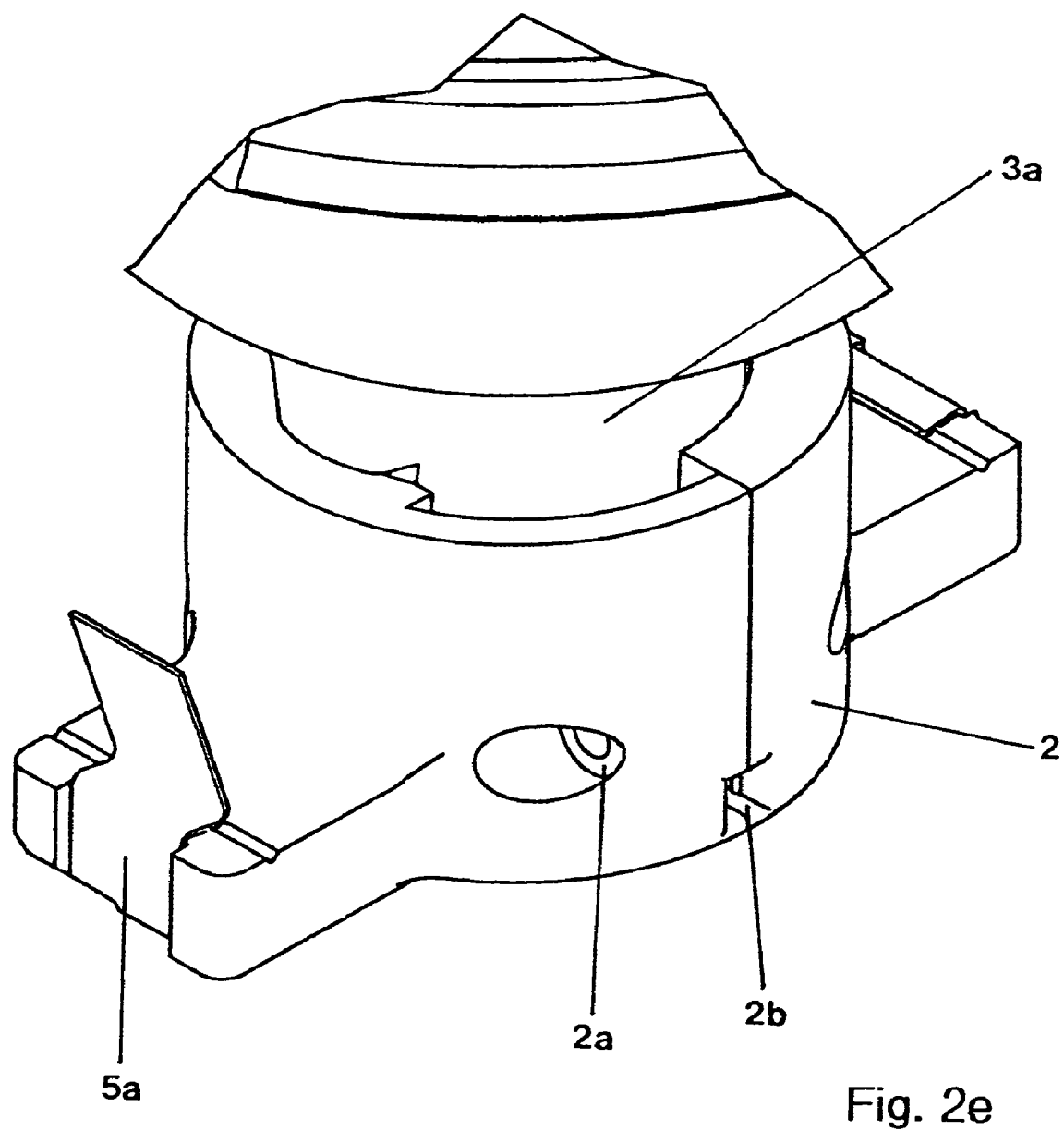

FIG. 2e shows the portion 2E of FIG. 2d in an enlarged view. Here, the bayonet catch between the reflector neck 3a and the lamp socket 2 can be seen clearly. Furthermore, there are openings 2b in the lamp socket 2, through which electrical connections of a UV emitter (not seen here, but arranged in the reflector body 3) are guided to both sides of the lamp socket 2.

Figure 3A:
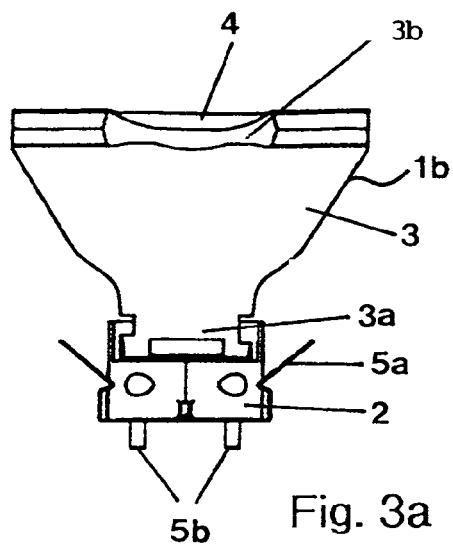
FIGS. 3a-3e show different views of another UV lamp arrangement of the invention with a round lamp socket.

FIG. 3a shows a UV lamp arrangement 1b in a side view with a two-part, round lamp socket 2 and a reflector body 3 made of glass. The outlet opening of the reflector body 3 for UV radiation is covered with a filter disk 4. Furthermore, the reflector body 3 has a reflector neck 3a, which is connected with the lamp socket 2 directly by a bayonet catch. In addition, in the region of the outlet opening of the reflector body 3 for UV radiation, there are half moon-shaped recesses 3b. Here, the filter disk 4 completely covers the reflector body 3, so that no opening remains. A spring 5a and also retaining screws 5b for mounting the UV lamp arrangement 1b in a tanning device are present on the lamp socket 2.

Figure 3B:
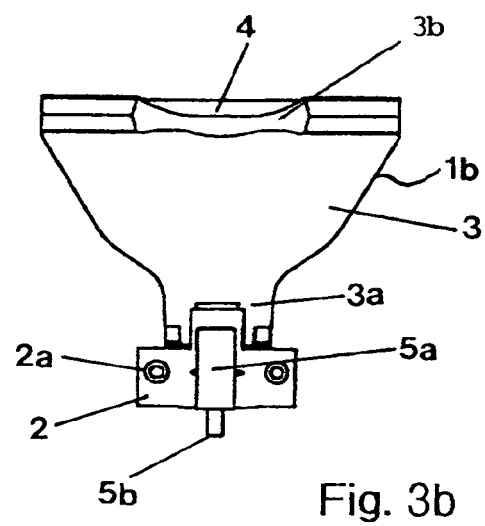

FIG. 3b shows the UV lamp arrangement 1b of FIG. 3a in another side view, but rotated by 90°. It can be seen that the two parts of the two-part lamp socket 2 are connected by rivets or screws 2a.

Figure 3C:
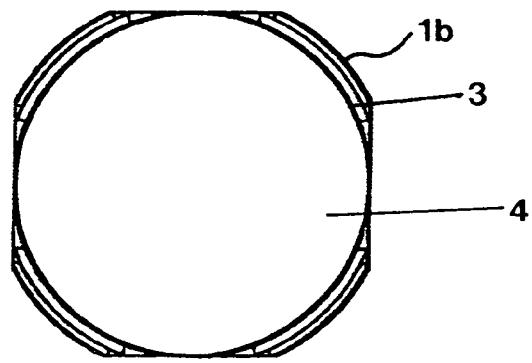

FIG. 3c shows the UV lamp arrangement 1b of FIGS. 3a and 3b in a top view.

Figure 3D:
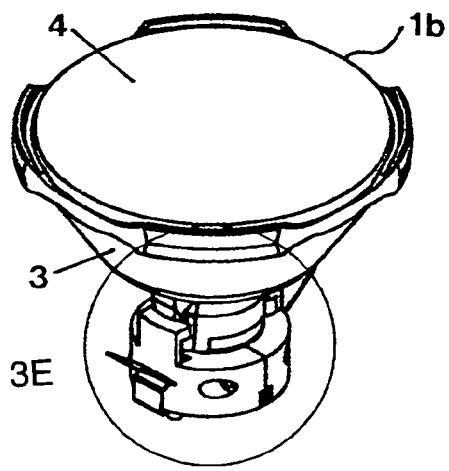

FIG. 3d shows the UV lamp arrangement 1b of FIGS. 3a-3c in a perspective view.

Figure 3E:
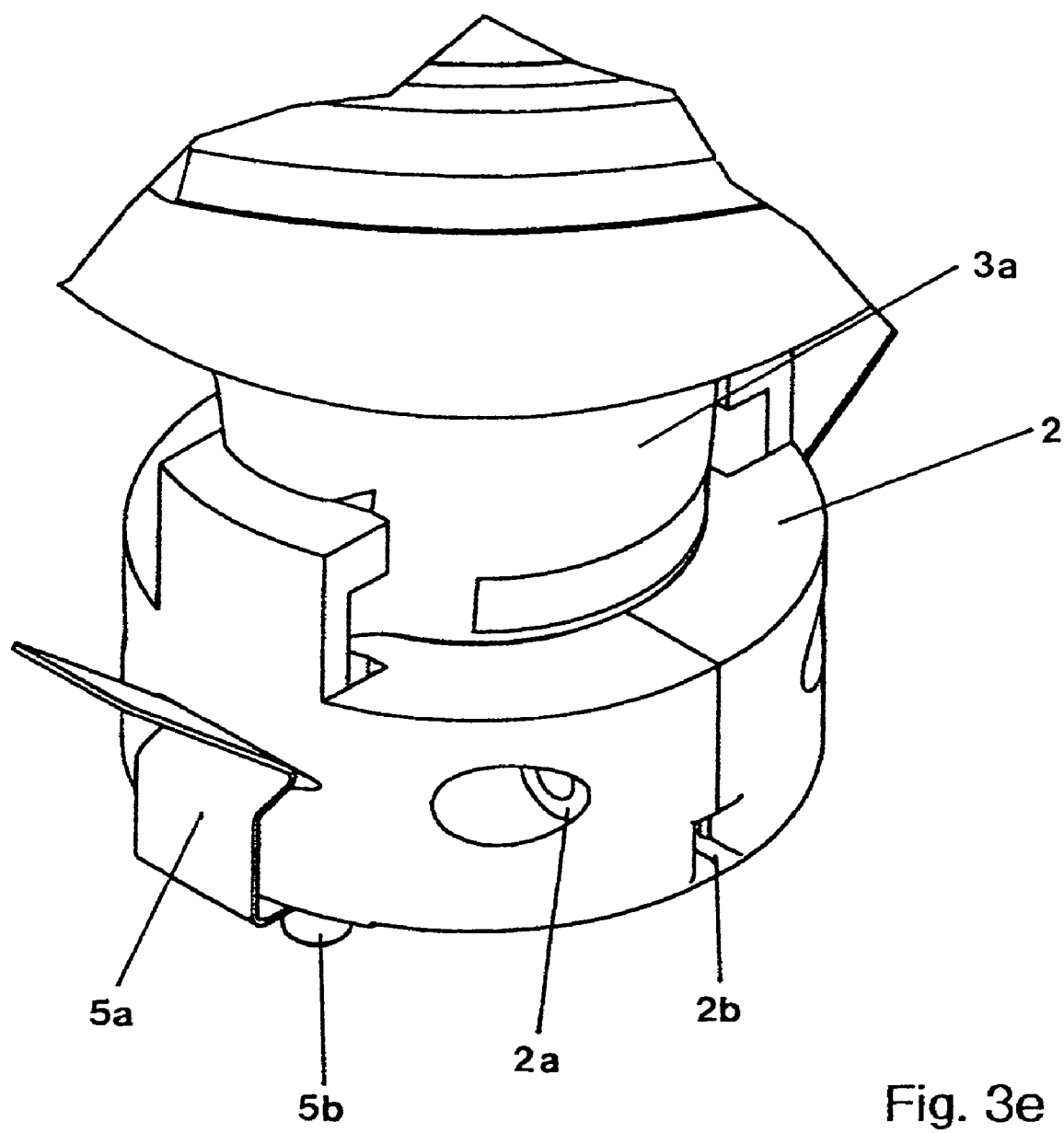

FIG. 3e shows the portion 3E of FIG. 3d in an enlarged view. Here, the bayonet catch between the reflector neck 3a and the lamp socket 2 can be seen clearly. Furthermore, there are openings 2b in the lamp socket 2, through which electrical connections of a UV emitter (not seen here, but arranged in the reflector body 3) are guided to both sides of the lamp socket 2.

Figure 4A:
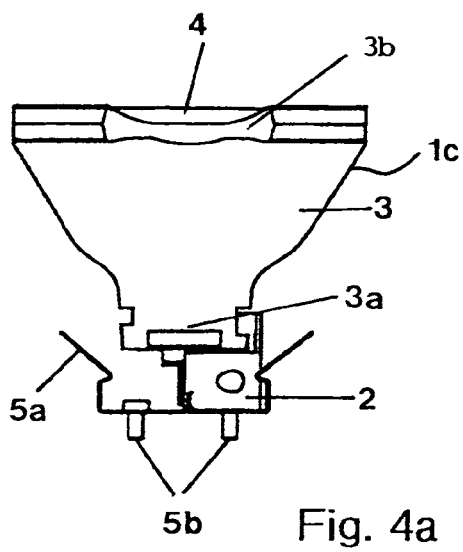

FIG. 4a shows a UV lamp arrangement 1c in a side view with a two-part, round lamp socket 2 and a reflector body 3 made of glass, wherein only half of the lamp socket 2 is shown. The outlet opening of the reflector body 3 for UV radiation is covered with a filter disk 4. Furthermore, the reflector body 3 has a reflector neck 3a, which is connected with the lamp socket 2 directly by a bayonet catch. In addition, half moon-shaped recesses 3b are arranged in the region of the outlet opening of the reflector body 3 for UV radiation. Here, the filter disk 4 completely covers the reflector body 3, so that no opening remains. A spring 5a and also retaining screws 5b for mounting the UV lamp arrangement 1c in a tanning device are present on the lamp socket 2.

Figure 4B:
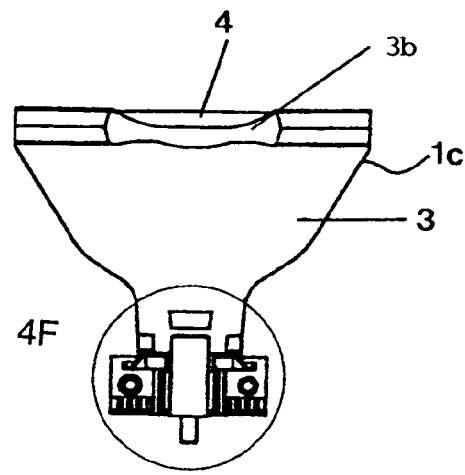

FIG. 4b shows the UV lamp arrangement 1c of FIG. 4a in another side view, but rotated by 90°. The interior of the lamp socket 2 can be seen.

Figure 4C:
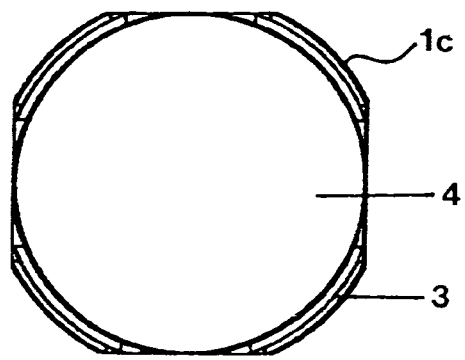

FIG. 4c shows the UV lamp arrangement 1c of FIGS. 4a and 4b in a top view.

Figure 4D:
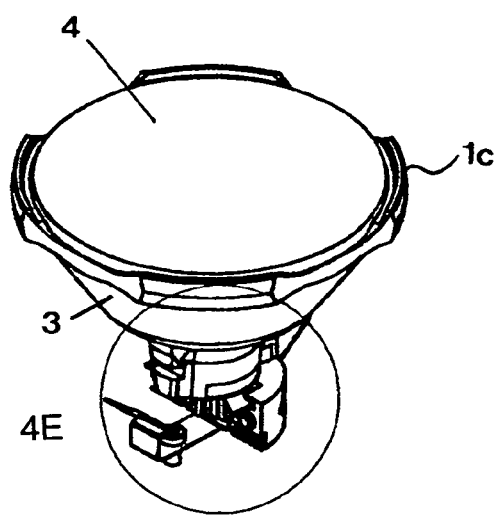

FIG. 4d shows the UV lamp arrangement 1c of FIGS. 4a-4c in a perspective view.

FIG. 4e shows the portion 4E of FIG. 4d in an enlarged view. Here, the reflector neck 3a with knobs 3c formed thereon for the bayonet catch can be seen clearly. Furthermore, the openings 2b in the lamp socket 2 can be seen, through which electrical connections of a UV emitter (not seen here, but arranged in the reflector body 3) are guided to both sides of the lamp socket 2. For fixing the reflector neck 3a in the lamp socket 2 there is a leaf spring 7, which presses the reflector body 3 upwards and thus fixes the bayonet catch.

FIG. 4f shows the portion 4F of FIG. 4b in an enlarged view. Again, the openings 2b in the lamp socket 2 can be seen, through which electrical connections of a UV emitter (not seen here, but arranged in the reflector body 3) are guided to both sides of the lamp socket 2. For fixing the reflector neck 3a in the lamp socket 2, there is the leaf spring 7, which presses the reflector body 3 upwards and fixes the bayonet catch.

Figure 5A:
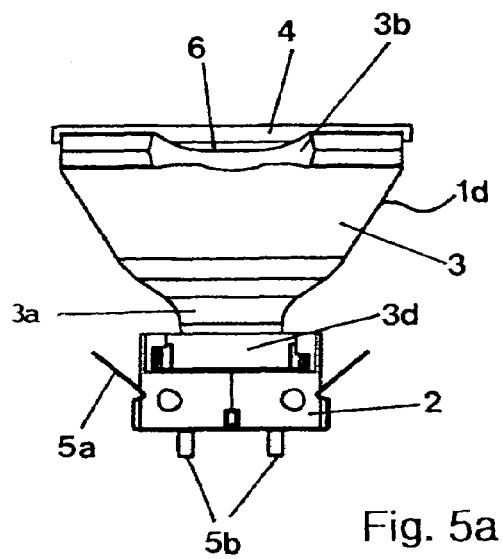
FIGS. 5a-5e show different views of another UV lamp arrangement of the invention with a round lamp socket.

FIG. 5a shows a UV lamp arrangement 1d in side view with a two-part, round lamp socket 2 and a reflector body 3 made of glass. The outlet opening of the reflector body 3 for UV radiation is covered with a filter disk 4. Furthermore, the reflector body 3 has a reflector neck 3a, on which is formed another component 3d, embodied as a ring. The component 3d, embodied as a ring, has knobs 3c (see FIG. 5e) and is connected with the lamp socket 2 directly by a bayonet catch. In addition, half moon-shaped recesses 3b are arranged in the region of the outlet opening of the reflector body 3 for UV radiation, such that openings 6 enable an exchange of air with the space in the reflector body 3. A spring 5a and also retaining screws 5b for mounting the UV lamp arrangement 1d in a tanning device are present on the lamp socket 2.

Figure 5B:
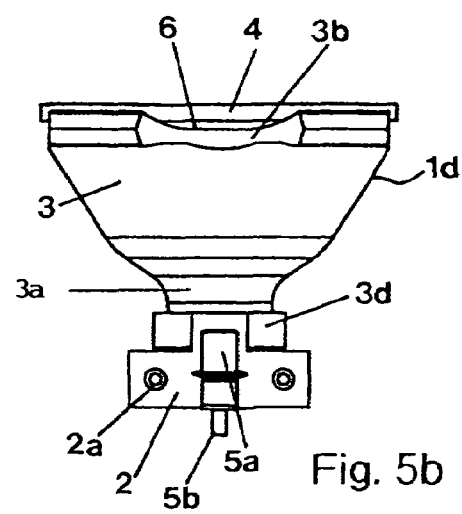

FIG. 5b hows the UV lamp arrangement 1d of FIG. 5a in another side view, but rotated by 90°. It can be seen that the two parts of the two-part lamp socket 2 are connected by rivets or screws 2a.

Figure 5C:
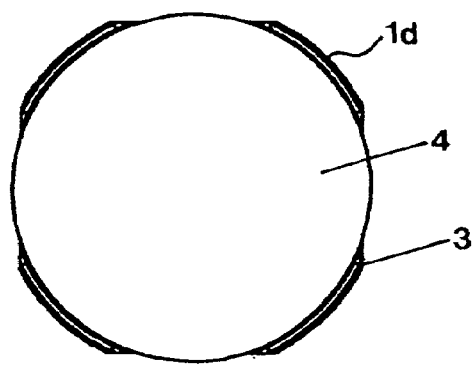

FIG. 5c shows the UV lamp arrangement 1d of FIGS. 5a and 5b in a top view.

Figure 5D:
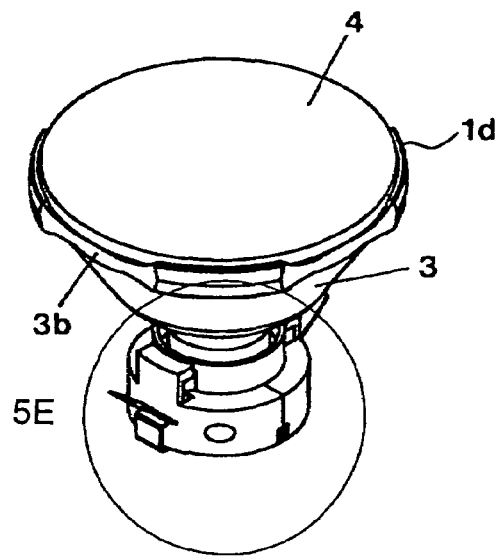

FIG. 5d shows the UV lamp arrangement 1d of FIGS. 5a-5c in a perspective view.

Figure 5E:
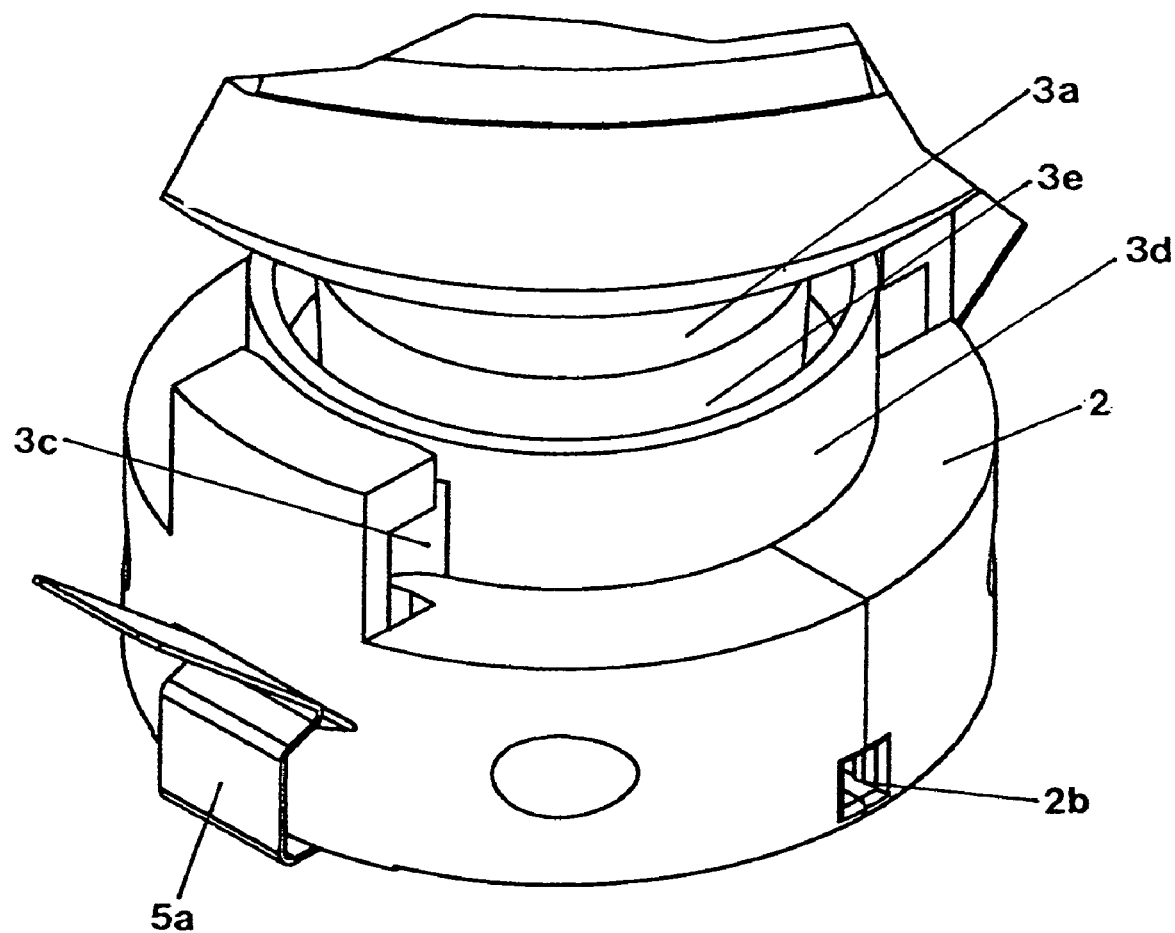

FIG. 5e shows the portion 5E of FIG. 5d in an enlarged view. Here, the bayonet catch between the component 3d, embodied as a ring, and the lamp socket 2 can be seen clearly. The reflector neck 3a is connected rigidly to the component 3d, embodied as a ring, in the region 3e by an adhesive (not shown here). Furthermore, there are openings 2b in the lamp socket 2, through which electrical connections of a UV emitter (not seen here, but arranged in the reflector body 3) are guided to both sides of the lamp socket 2.

Figure 6A:
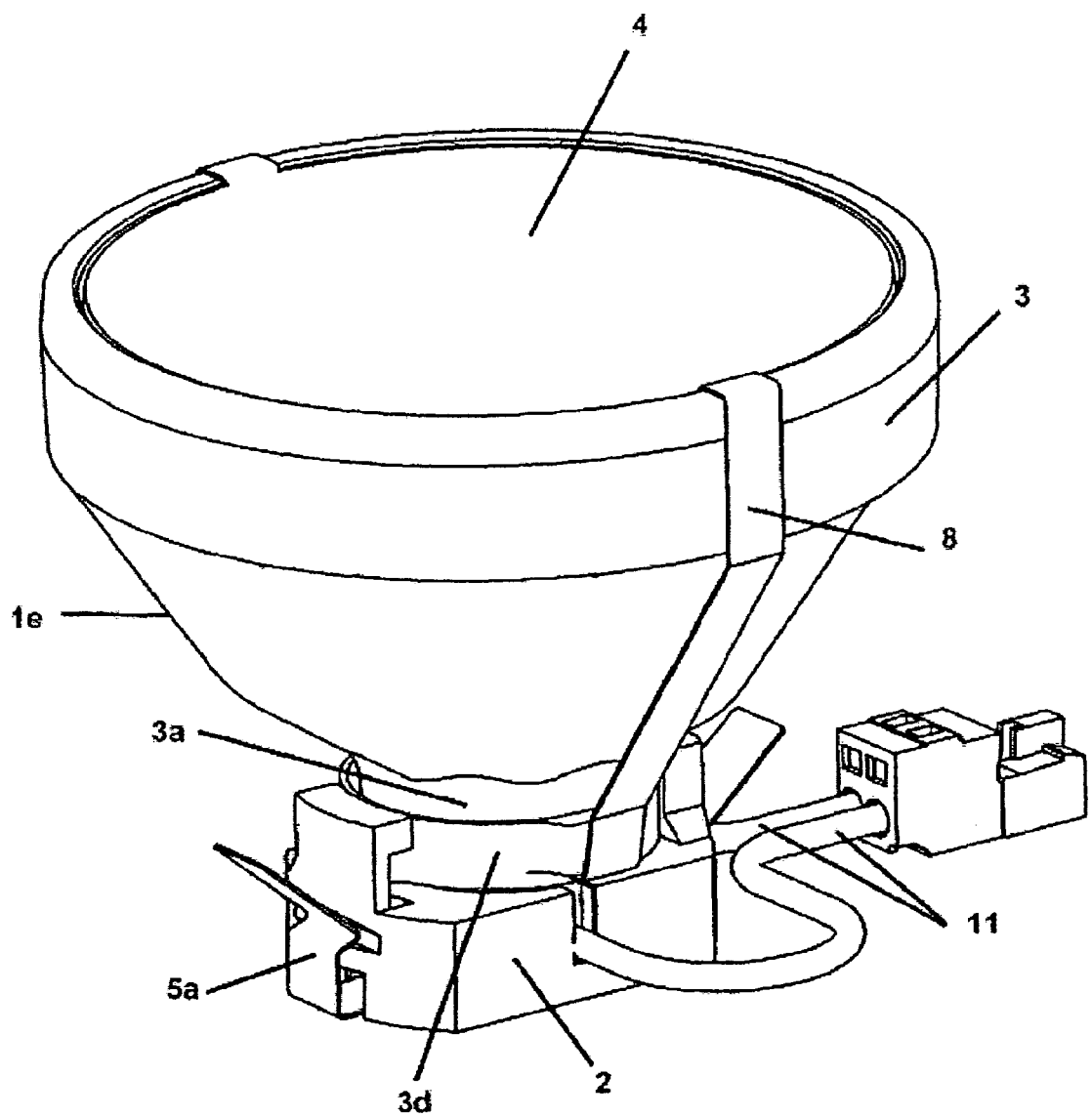

FIG. 6a shows a UV lamp arrangement 1e in a perspective view with a one-part, elongated lamp socket 2, rounded on the short sides, and a reflector body 3 made of glass. The outlet opening of the reflector body 3 for UV radiation is covered with a filter disk 4. Furthermore, the reflector body 3 has a reflector neck 3a, on which another component 3d, embodied as a ring, is formed and which is connected with the lamp socket 2 directly by a bayonet catch. Two clamps, embodied as gripping arms 8, here represent a mechanical connection between the reflector body 3 and the ring 3d. A spring 5a for mounting the UV lamp arrangement 1e in a tanning device is present on the lamp socket 2.

Figure 6B:
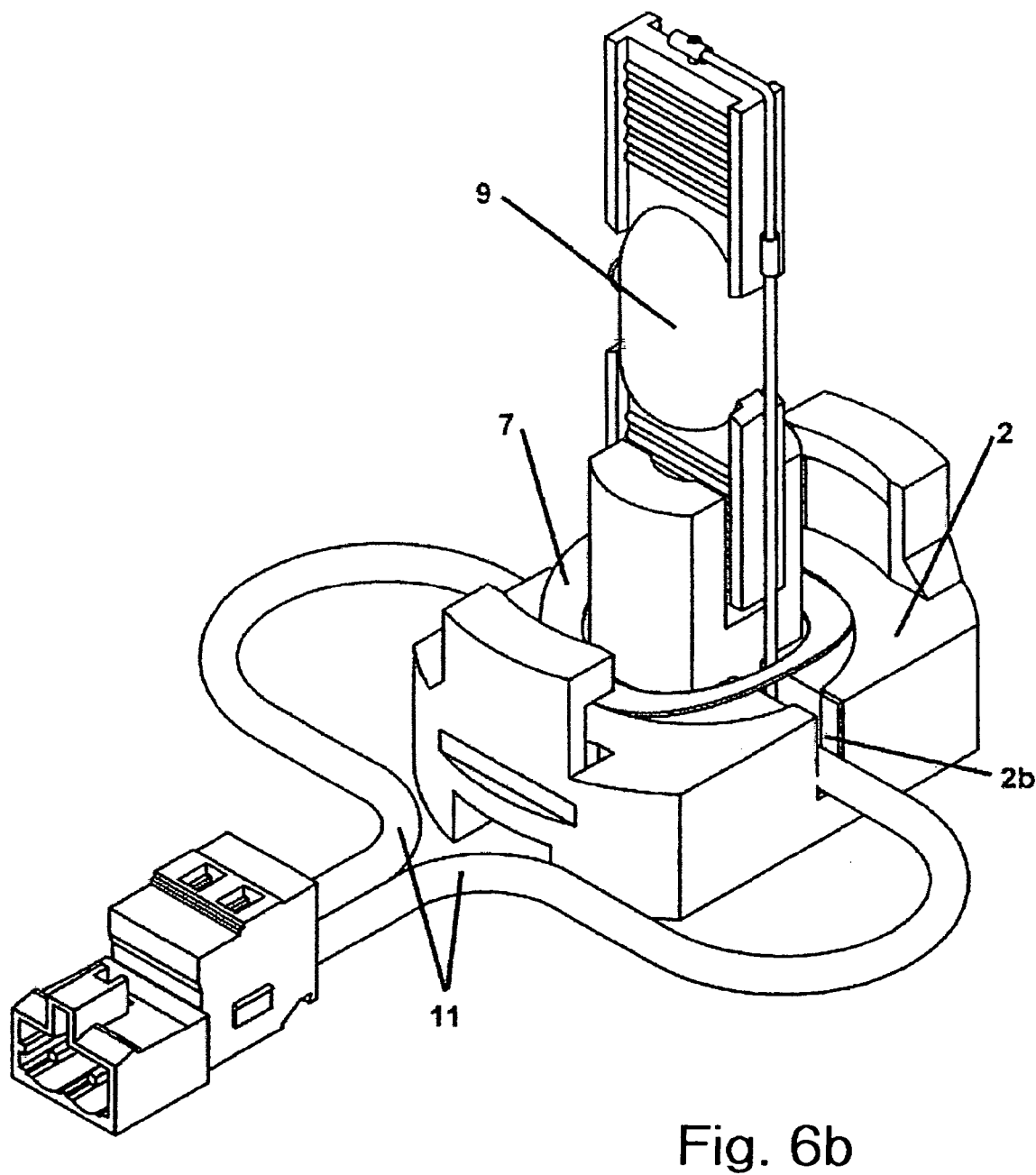

FIG. 6b shows a UV lamp arrangement of FIG. 6a in a perspective view with a one-part, elongated lamp socket 2, rounded on the sides, (without the reflector body 3 made of glass). The emitter 9 in the lamp socket 2 can be seen clearly with the leaf spring 7, which presses the reflector body 3 (when present) upwards and thus fixes the bayonet catch. In the lamp socket 2, the side openings 2b can be seen, through which the electrical connections 11 of the UV emitter 9, which can be seen here and which is arranged in the reflector body, are guided to both sides of the lamp socket 2.

Figure 7:
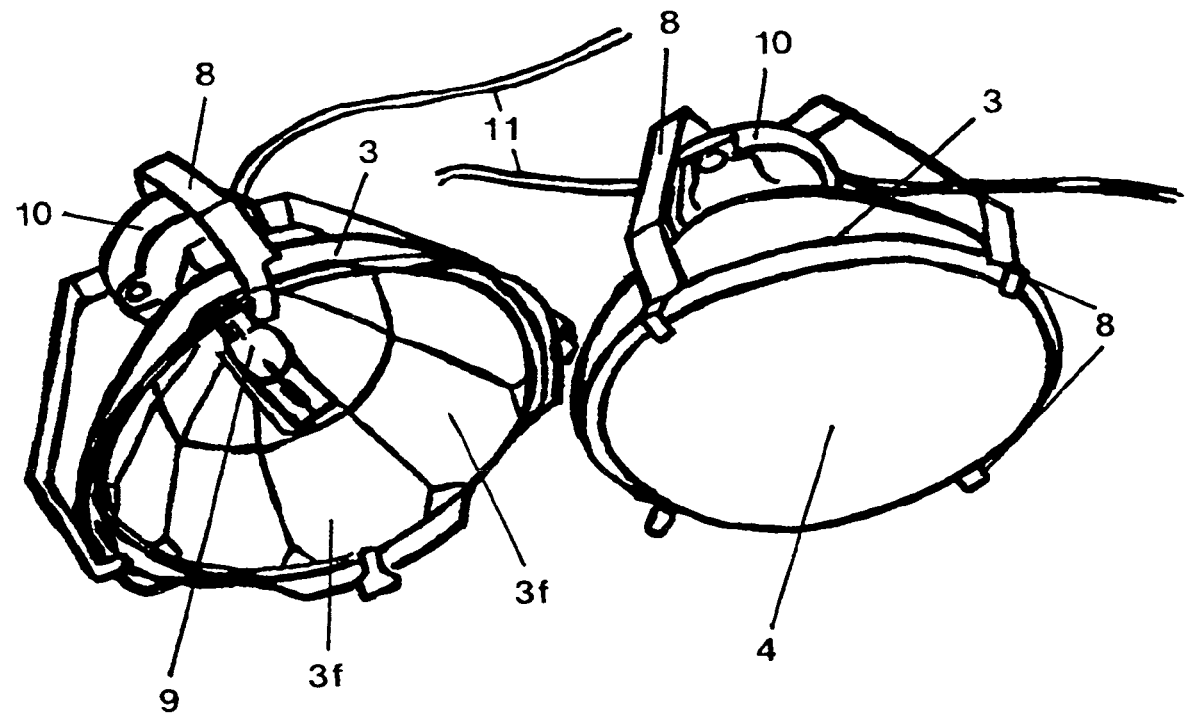
FIG. 7 is a perspective view of two UV lamp arrangements of the invention, each with four gripping arms made of bent strips of sheet metal.
Figure 8:
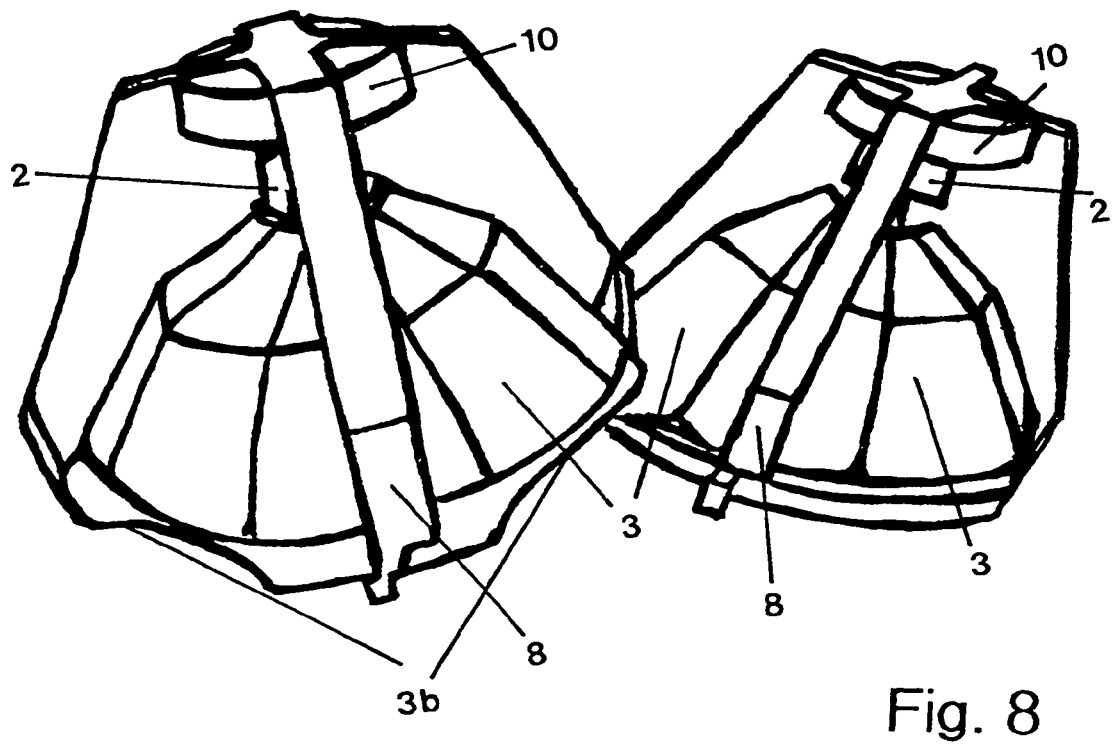
FIG. 8 is another perspective view of the UV lamp arrangements of FIG. 7.

FIGS. 7 and 8 show perspective views of two UV lamp arrangements, each having a lamp socket 2 and a concave reflector body 3. The right-hand arrangement of the two UV lamp arrangements of FIG. 7 shows a filter disk 4 on the reflector body 3. In contrast, the left-hand arrangement of the two UV lamp arrangements of FIG. 7 shows no filter disk 4 on the reflector body 3, so that the UV emitter 9 is visible within the cavity of the reflector body 3. The reflector body 3 is held by four gripping arms 8, which are formed of bent strips of sheet metal and enable simple disassembly of the reflector body 3 and filter disk 4 and thus an exchange of the UV emitter 9. The reflector body 3 is constructed of facets 3f. The left-hand UV lamp arrangement of FIG. 8 further shows on the reflector body 3 half moon-shaped recesses 3b, which enable an exchange of air between the space inside the reflector body 3 and the space outside the reflector body 3 after assembly of a filter disk. The electrical connection of the UV emitter 9 with the lamp socket 2 is realized by the mount 10 with the electrical connection wires 11.

Figure 9:
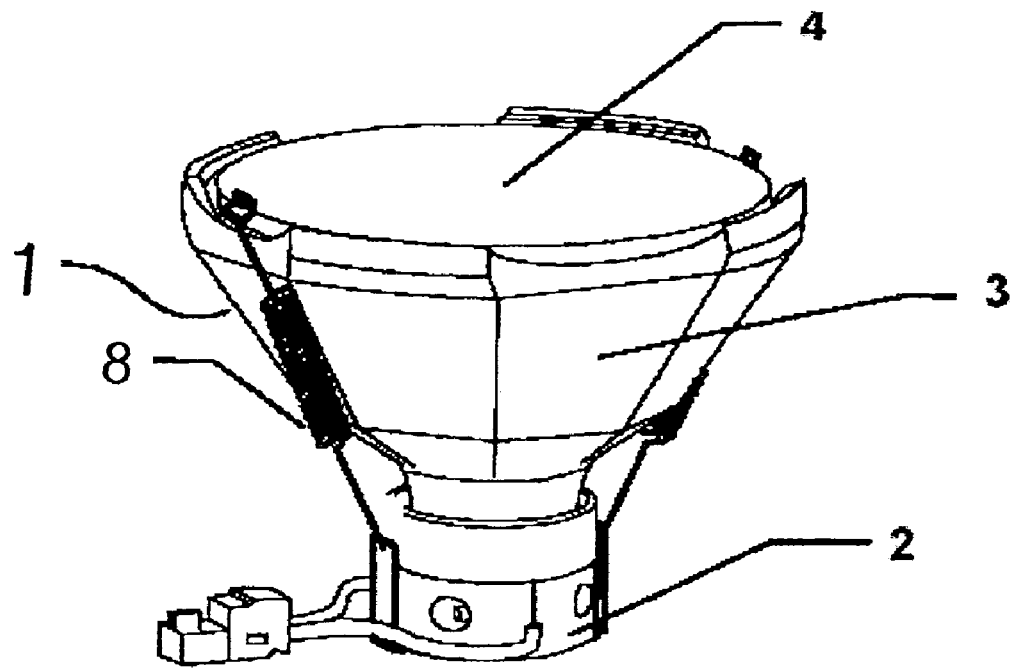
FIG. 9 is a perspective view of one configuration of the invention, in which the gripping arms are embodied so that they press the socket against the reflector at the emitter inlet opening of the reflector with spring tensile force.

FIG. 9 shows a UV lamp arrangement 1 in perspective view, in which the gripping arms 8 are embodied so that they press the socket 2 at the reflector outlet opening with spring tensile force against the reflector 3.

Figure 10:
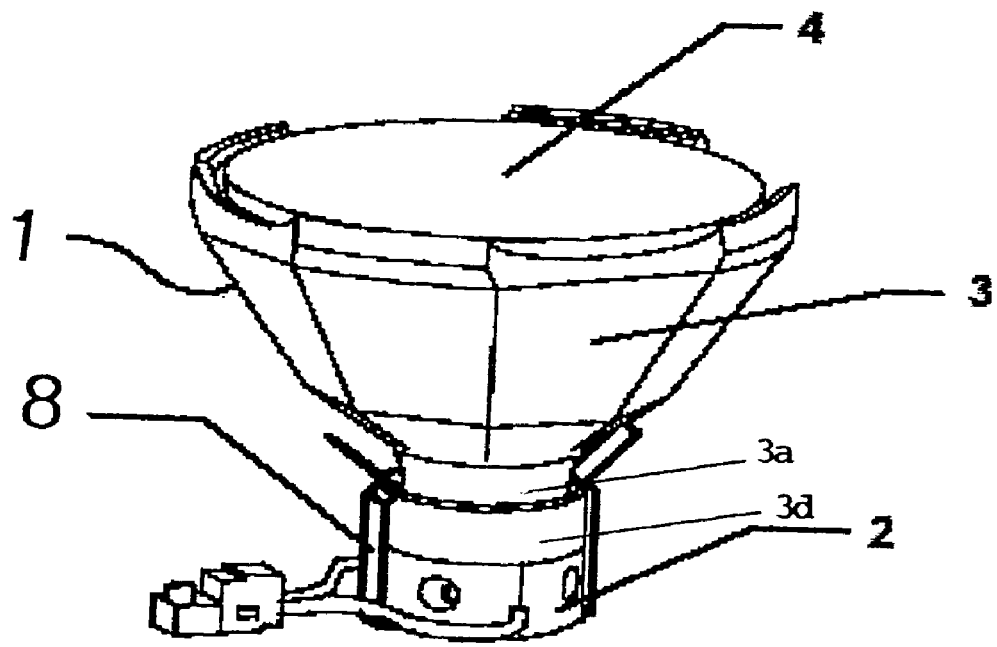
FIG. 10 is a perspective view of a lamp arrangement of the invention, in which a socket with two gripping arms is held on the reflector body; here, the gripping arms are embodied so that they clamp the socket against the reflector neck.

FIG. 10 shows a lamp arrangement 1, in which a socket 2 is held on the reflector body 3 with two gripping arms 8. Here, the gripping arms 8 are formed such that they clamp the socket 2 against the reflector neck 3a or the component 3d embodied as a ring.

Figure 11:
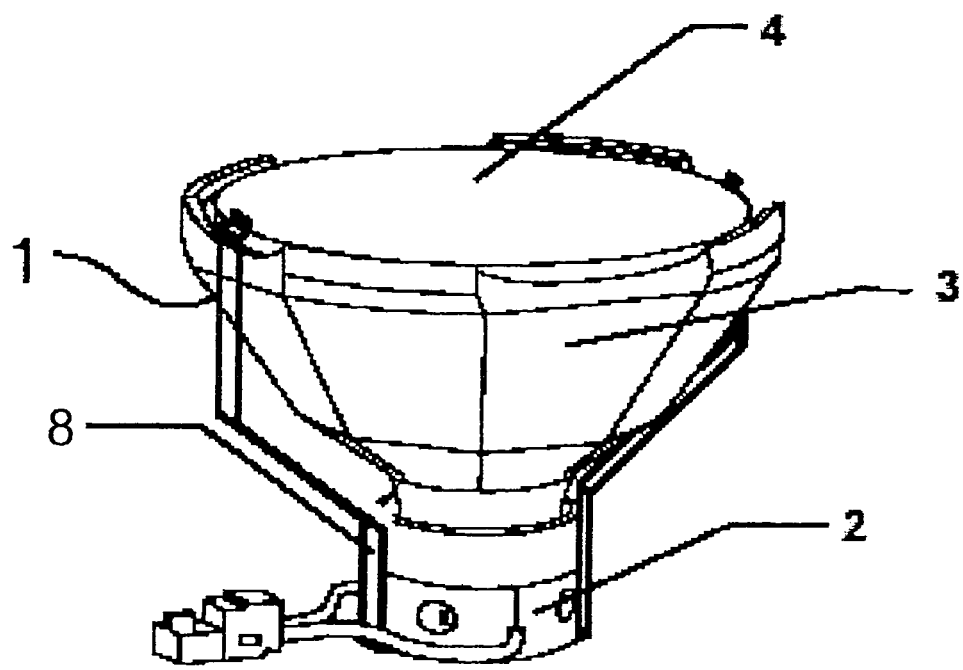
FIG. 11 is a perspective view of one configuration of the invention, in which the gripping arms are embodied as clamps, which press the socket against the reflector, wherein the gripping arms engage in the reflector opening.

FIG. 11 shows a lamp arrangement 1, in a perspective view, in which the gripping arms 8, similar to FIG. 8, are embodied as clamps, which press the socket 2 against the reflector 3, wherein the gripping arms 8 engage in the reflector opening.

Figure 12:
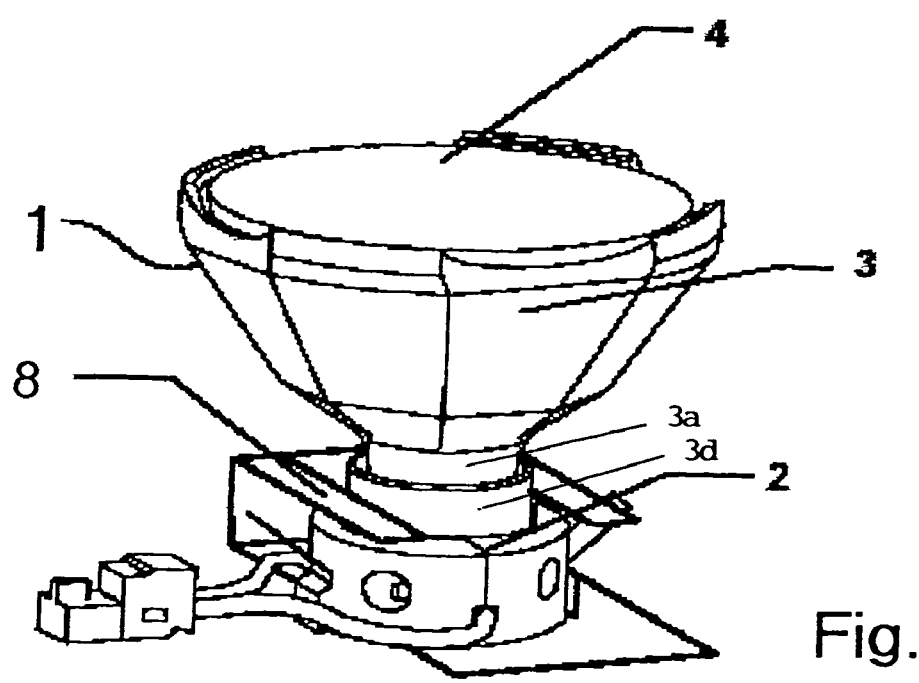
FIG. 12 is a perspective view of a lamp arrangement of the invention, in which a socket is held on the reflector body with gripping arms; here, the gripping arms are embodied so that they clamp the socket against the reflector neck.

FIG. 12 shows a lamp arrangement 1, in which a socket 2 is held on the reflector body 3 with two gripping arms 8. Here, the gripping arms 8 are constructed as U-profiled clamps, which clamp the socket 2 against the reflector neck 3a or a component 3d embodied as a ring.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A UV lamp arrangement (1) comprising
a lamp socket (2), a reflector body (3) arranged on the lamp socket (2) and having a reflector neck (3a), wherein the reflector neck (3a) and the reflector body (3) are formed of a same material and in one piece, wherein the reflector neck (3a) is connected with a ring component (3d) having knobs (3c) thereon, such that the ring component (3d) is directly connectable with the lamp socket (2), and wherein the ring component (3d) is connected with the reflector neck (3a) by glass solder or adhesive; and an emitter (9) arranged inside the reflector body (3) and on the lamp socket (2), wherein the reflector body (3) is detachably connected with the lamp socket (2) by a bayonet catch, such that the reflector body (3) is detachable from the lamp socket (2) separately from the emitter (9).

2. The lamp arrangement (1) according to claim 1, wherein the reflector body (3) comprises facets (3f).

3. The lamp arrangement (1) according to claim 1, wherein the reflector body (3) is connected with a filter disk (4), which covers an outlet opening of the reflector body (3) for optical radiation.

4. The lamp arrangement (1) according to claim 3, wherein the filter disk (4) is connected with the reflector body (3) by an elastic adhesive or a clamp.

5. The lamp arrangement (1) according to claim 3, wherein the filter disk (4) completely closes the outlet opening of the reflector body (3).

6. The lamp arrangement (1) according to claim 1, wherein the emitter (9) is a UV emitter.

7. The lamp arrangement (1) according to claim 6, wherein the reflector body (3) has a UV radiation-reflective coating.

8. The lamp arrangement (1) according to claim 6, wherein the reflector body (3) comprises glass or glass ceramic and has a coating transparent to infrared radiation.

9. The lamp arrangement (1) according to claim 6, wherein the UV emitter (9) is a metal halide emitter.

10. The lamp arrangement (1) according to claim 1, wherein the lamp arrangement operates within in a power range of about 100 W to 300 W without forced-air cooling.

11. The lamp arrangement according to claim 1, having at least one UV lamp arrangement (1) mounted in a tanning device.

12. A UV lamp arrangement (1) comprising a lamp socket (2), a reflector body (3) arranged on the lamp socket (2) and having a reflector neck (3a), wherein the reflector neck (3a) and the reflector body (3) are formed of a same material and in one piece, wherein reflector neck 3(a) is connected with a ring component (3d) having knobs (3c) thereon, such that the ring component (3d) is directly connectable with the lamp socket (2), and wherein the ring component (3d) is shrunk onto the reflector neck (3a); and an emitter (9) arranged inside the reflector body (3) and on the lamp socket (2), wherein the reflector body (3) is detachably connected with the lamp socket (2) by a bayonet catch such that the reflector body (3) is detachable from the lamp socket (2) separately from the emitter (9).

* * * * *